US006428824B1

(12) United States Patent
Zheng et al.

(10) Patent No.: US 6,428,824 B1
(45) Date of Patent: Aug. 6, 2002

(54) **TREATMENT OF SEXUAL DYSFUNCTION WITH AN EXTRACT OF *LEPIDIUM MEYENII* ROOTS**

(75) Inventors: Bo Lin Zheng, Wayne; Calvin Hyungchan Kim; Stephen Wolthoff, both of Fort Lee; Kan He, River Edge; Lingling Rogers, Parsipanny; Yu Shao, Riveredge; Qun Yi Zheng, Wayne, all of NJ (US)

(73) Assignee: Pure World Botanicals, Inc., South Hackensack, NJ (US)

( * ) Notice: Subject to any disclaimer, the term of this patent is extended or adjusted under 35 U.S.C. 154(b) by 0 days.

(21) Appl. No.: 10/002,757

(22) Filed: Oct. 19, 2001

Related U.S. Application Data

(62) Division of application No. 09/878,141, filed on Jun. 8, 2001, which is a division of application No. 09/261,806, filed on Mar. 3, 1999, now Pat. No. 6,267,995.

(51) Int. Cl.$^7$ ................................................ A61K 35/78
(52) U.S. Cl. ........................................ 424/773; 424/725
(58) Field of Search ................................. 424/725, 773

(56) References Cited

FOREIGN PATENT DOCUMENTS

JP 8-12565 A 6/1996

OTHER PUBLICATIONS

Leon, J., Economic Botany, 18, pp. 122–127 (1964).
Quirós and Cárdenas, Maca (*Lepidium meyenii* Walp.), International Plant Genetic Resources Institute, pp. 175–197 (1997).
Johns, T., Journal of Ethnobiology, 1, pp. 208–212 (1981).
Steinberg, P. et al., Phil Steinberg's Cat's Claw News, 1(2) (1995).
Dini, A. et al., Food Chemistry, 49, Chemical composition of *Lepidium meyenii*. pp. 347–349 (1994).
Comas, M. et al., Alimenteria, 97, Estudio Bromatologico De La Maca O Paca (*Lepidium meyenii*), pp. 85–90 (1996).
Barstaw, L.E. et al., J. Org. Chem., 36, 1305 (1971).

*Primary Examiner*—David M. Naff
*Assistant Examiner*—Mike Meller
(74) *Attorney, Agent, or Firm*—Dechert

(57) ABSTRACT

An isolated composition obtained by extracting *Lepidium meyenii* roots is provided. The composition is substantially free of cellulose and comprises between about 5% and about 9% of benzyl isothiocyanate, between about 1% and about 3% of Lepidium sterol component, between about 20% and about 30% of Lepidium fatty acid component, and about 10% or more of macamide component. The composition is prepared by a process which comprises contacting Lepidium meyenii roots with a first aqueous solvent of about 90% vol-% or more water, then separating the residual *Lepidium meyenii* root material from the first contacted aqueous solvent, then contacting the residual *Lepidium meyenii* root material with a second aqueous solvent which comprises a mixture of an alcohol and water having about 90 vol-% alcohol or more to form a liquor, and then finally concentrating the liquor to obtain the composition. The composition can be used for treating cancer and sexual dysfunction.

10 Claims, No Drawings

US 6,428,824 B1

TREATMENT OF SEXUAL DYSFUNCTION WITH AN EXTRACT OF LEPIDIUM MEYENII ROOTS

This application is a divisional application of U.S. application Ser. No. 09/878,141, filed Jun. 8, 2001, which is a divisional application of U.S. application Ser. No. 09/261, 806, filed Mar. 3, 1999, now U.S. Pat. No. 6,267,995 B1, the disclosures of which are both herein incorporated by reference in their entirety.

The present invention relates to compositions containing particular components that can be obtained from a plant which can have pharmaceutical applications. More particularly, the plant genus is Lepidium.

Lepidium meyenii, commonly called maca or Peruvian ginseng, is a perennial plant having a fleshy, edible, tuberous root. Another species is Lepidium peruvianum. The maca root is consumed for food and is also consumed for its pharmacological properties; for example to enhance fertility. (See Leon, J., Economic Botany, 18:122–127(1964)) Maca has also been used to treat chronic fatigue. (Steinberg, P., Phil Steinberg's Cat's Claw News, Vol. 1, Issue 2, July/August (1995).

Johns, *Ethnobiology*, 1:208–212(1981), studied the biologically active aromatic glycosinolates present in the plant and also reported that benzyl isothiocyanate was the principal isothiocyanate in the plant, with p-methoxybenzyl isothiocyanate being present in relatively smaller amount. The role of these species in reproduction was discussed.

Dini et al., *Food Chem.*, 49:347–349(1994) described the total content of carbohydrates and amino acids (free and from protein hydrolysis) and listed 20 saturated and unsaturated paraffinic acids (principally linoleic, palmitic, and oleic acids) present in the plant. A sterol fraction containing five sterols (identified as their acetates) was also reported. An alkaloid fraction was reported but not characterized.

SUMMARY OF THE INVENTION

In one aspect, the present invention relates to an isolated, Lepidium-derived composition that is essentially free of cellulose and lignin and that has about 40% of polysaccharides that can be isolated from Lepidium plant material (a Lepidium polysaccharide component). The composition can also contain an aqueous component and a component, designated a Lepidium amino acid component, having amino acids that can be isolated from Lepidium plant material and. Typically, the Lepidium amino acid component has about 70% or more proline, 5% or more glutamic acid, and 5% or more valine. In certain embodiments, the composition has about 0.3% benzyl isothiocyante and about 0.5% of a component, called a macamide component, having amides of fatty acids that can be isolated from Lepidium material. In an particular embodiment, the composition has about 45% or more of a Lepidium polysaccharide component. In another embodiment, the composition is combined with one or more pharmaceutically acceptable excipients.

In another aspect, the present invention relates to a composition having about 0.3% or more benzyl isothiocyanate, about 0.3% or more of a macamide component, about 1% or more of fatty acids that can be isolated from Lepidium plant material (a Lepidium fatty acid component), and about 0.15% of sterols that can be isolated from Lepidium plant material (a Lepidium sterol component). In a preferred embodiment, the composition has between about 2% and about 5% benzyl isothiocyanate, about 0.2% and about 1% Lepidium sterol component, between about 10% and about 20% Lepidium fatty acid component, and about 3% to about 7% macamide component. In a particularly preferred embodiment, the composition has between about 5% and about 9% benzyl isothiocyanate, between about 1% and about 3% of Lepidium sterol component, between about 20% and about 30% of a Lepidium fatty acid component, and about 10% or more of macamide component. One or more of the foregoing compositions can be combined with a pharmaceutically acceptable excipient.

In another aspect, the invention relates to novel fatty acid amides: N-benzyl, octanamide having the chemical formula $C_{15}H_{23}NO$, N-benzyl-16(R,S)-hydroxy-9-oxo-10E,12E, 14E-octadecatrieneamide having chemical formula $C_{35}H_{25}NO_3$, and N-benzyl-16(S)-hydroxy-9-oxo-10E,12E, 14E-octadecatrieneamide having the chemical formula $C_{25}H_{35}NO_3$.

In yet another embodiment, the present invention relates to a process of obtaining an isolated Lepidium-derived composition including the steps of:
   a) contacting Lepidium plant material with an aqueous solvent,
   b) separating the contacted aqueous solvent from the Lepidium plant material, and
   c) concentrating the composition of step b) to isolate the composition.

Preferably, the aqueous solvent is water. More preferably, the aqueous solvent is a mixture of alcohol, preferably SDA, and still more preferably, a mixture of 75 vol-% SDA and 25 vol-% water.

In yet other embodiments, the process includes the further steps of:
   d) applying the first Lepidium composition from step c) to a reverse phase liquid chromatography column,
   f) eluting the reverse phase chromatography column with a first elution volume of aqueous solvent effective to elute a first effluent from which a composition having about 45% or more Lepidium polysaccharide component is isolated by, for example, concentration.

In yet another embodiment, the invention process includes the further step of g), eluting the reverse phase chromatography column with a second elution volume of aqueous solvent to form a second effluent from which the composition can be isolated by, for example, the step of concentrating the second effluent.

In a preferred embodiment, the second elution volume has two or more gradient volumes that are sequentially eluted and the resulting second effluent is fractionate collected as gradient fractions so that at least one gradient fraction is collected for each gradient volume eluted. The gradient fractions can be combined and concentrated to obtain an isolated Lepidium derived composition that has about 0.3% or more of benzyl isothiocyanate, about 0.15% or more Lepidium sterol component, about 1% or more Lepidium fatty acid component, and about 0.3% or more of macamide component. Preferably, each of the two or more gradient volumes comprises a mixture of an alcohol and water and wherein the vol-% alcohol in the first gradient volume is about 20 vol-% or more and the vol-% alcohol in any subsequent gradient volume is equal to or greater than the vol-% alcohol in the immediately previously eluted gradient volume.

In yet another embodiment, the invention provides a process for producing the composition having between about 5% and about 9% of benzyl isothiocyanate, between about 1% and about 3% of Lepidium sterol component, between about 20% and about 30% of Lepidium fatty acid component, and d) about 10% or more of macamide component comprising the steps of:

a) contacting Lepidium plant material with an aqueous solvent comprising about 90 vol-% or more water, c) concentrating the contacted aqueous solvent to make a residue of Lepidium plant material, d) contacting the residue of Lepidium plant material with aqueous solvent comprising a mixture of an alcohol and water having about 90 vol-% alcohol or more to form a liquor, and e) concentrating the liquor to obtain the composition.

The preferred plant material in any embodiment is *Lepidium meyenii*.

In still another embodiment, the present invention relates to a method of treating or preventing cancer in an animal, preferably a human, by administering a cancer treating or preventing effective amount of any of the hereinabove described isolated Lepidium-derived compositions. In another embodiment, the present invention relates to a method for treating sexual dysfunction in an animal, preferably a human, by administering a sexual dysfunction treating or preventing amount of any of the hereinabove described isolated Lepidium-derived compositions to the animal. In a preferred embodiment, the animal is a female animal and the sexual dysfunction is infertility. In a more preferred embodiment, the animal is a male animal and the sexual dysfunction is a sub-normal libido. In a yet more preferred embodiment, the animal is a male animal and the sexual dysfunction is impotence.

DETAILED DESCRIPTION

As used herein, the following terms have the following meanings.

Alcohol: The term alcohol refers to a lower aliphatic alcohol having from one to six carbon atoms.

Aqueous component: This term refers to that part or portion of a composition that is made-up of one or more aqueous solvents.

Aqueous solvent: The term aqueous solvent means water or a single phase having an organic solvent that is miscible with water. Examples of miscible organic solvents include but are not limited to methanol, ethanol, isopropanol, n-propanol, acetone, and acetonitrile. Other miscible organic solvents are known to the skilled artesian.

Benzyl isothiocyante: includes benzyl isothiocynate and its methoxy derivatives.

Column volume: Column volume refers to the volume of the space defined by the inner surface of the chromatography column or chamber that surrounds the stationary phase or a reverse phase chromatography column. Column volume is abbreviated herein as CV.

Fractionate collecting: When used in connection with an effluent or a gradient effluent, or a gradient fraction, the term fractionate collecting denotes that the effluent or gradient effluent is segregated into at least two portions or aliquots.

Lepidium amino acid component: This term refers to that part or portion of a composition that is made-up of amino acids that can be isolated from Lepidium plant material.

Lepidium composition: A Lepidium composition is a composition having at least one of a Lepidium amino acid component, a Lepidium fatty acid component, a Lepidium polysaccharide component, or a macamide component.

Lepidium fatty acid component: This term refers to that part or portion of a composition that is made-up of fatty acids that can be isolated from Lepidium plant material.

Lepidium plant material: As used herein, Lepidium plant material refers to plant matter from any part of a plant of the genus Lepidium. Examples of Lepidium plant matter include, but are not limited to, matter from *Lepidium meyenii* and *Lepidium peruvianum*.

Lepidium polysaccharide component: This term denotes that part or portion of a composition that is made-up of polysaccharides that can be isolated from Lepidium plant material.

Lepidium sterol component: As used herein, the term refers to that part or portion of a composition that is made-up of sterols that can be isolated from Lepidium plant material.

Macamide: Means amides and N-substituted amides of fatty acids that can be isolated from Lepidium plant material.

Percent (%): Unless otherwise limited or modified, percents and percentages described herein are on a weight basis. The chemical composition of plant material from a particular plant species varies with, for example, the conditions under which the plant is grown (for example soil and climate). A particular compound or mixture of compounds can exhibit pharmacological efficacy over a readily ascertainable range of composition and dosage. Therefore, it is understood that the percentages recited throughout are meant to include such variations outside the stated percentage or percentage ranges as would be anticipated by the skilled artesian.

Substantially Free of cellulose: Means having 5% or less of cellulose and lignin combined.

SDA: Means special denatured alcohol, typically a mixture of 97% to 95% ethanol with 3% to 5% of methanol or coal tar.

First Lepidium compositions of the invention can be obtained from an extraction composition in a first process. Starting material for a first process is Lepidium plant material, preferably *Lepidium meyenii*. Lepidium plant material, for example the root of *Lepidium meyenii*, is reduced in size to pieces having nominal dimensions between about 0.1 mm and 30 mm. The pieces of Lepidium plant material are contacted with aqueous solvent. The contacting in this or any embodiment may be by any suitable means as are known in the art; for example, percolation, vat extraction, counter current extraction, and the like. The contacting is for a time from about 2 hr. to about 18 hr. The contacting is carried out at a temperature above the solidification temperature (or where applicable the phase separation temperature) but below the boiling point of the aqueous solvent. Typically, the contacting is conducted from 20° C. to 75° C., with 40° C. to 50° C. being preferred. After the contacting, the aqueous solvent, which is an extraction composition containing a first Lepidium composition, is separated from residual plant material and the extraction composition is concentrated until the extrtaction composition has a solids component generally of at least about 70%, of which typically 40% is a Lepidium polysaccharide component. In this or any embodiment, the concentration can be by any of the means as are known in the art such as evaporation, distillation, and lyophilization, to mention a few.

First Lepidium compositions generally have 30% or more, preferably about 40% or more, of a Lepidium polysaccharide component and about 1% or more of a macamide component. Typically, 70% or more of the polysaccharide units of a polysaccharide of a Lepidium polysaccharide component are sucrose units. A macamide component includes N-benzyl octanamide (macamide A), N-benzyl-16-hydroxy-9-oxo-10E,12E,14E-octatrieneamides (macamide B), and N-benzyl-9,16-dioxo-10E,12E,14E-octadecatrieneamide (macamide C). First Lepidium compositions further contain about 8% or more of a Lepidium amino acid component. The Lepidium amino acid component of a first Lepidium composition typically has 70% or more proline, 5% or more glutamic acid, and 5% or more valine. First Lepidium compositions also generally contain up to 1% of benzyl isothiocyanate. First Lepidium compositions can also contain about 0.5% to about 1.5% Lepidium fatty acid component. First Lepidium compositions of the present invention are useful for their nutritional value and are useful for the treatment or prophylaxis of carcinomas. First Lepidium compositions are also useful for treating sexual dysfunction in particular sub-normal libido and impotence in males and infertility in women.

In a first process of the present invention, the composition of the extraction composition and the composition of the first Lepidium composition obtained therefrom can be changed by changing the aqueous solvent. When the aqueous solvent is an alcohol-water mixture having 75 vol-% SDA, the first Lepidium composition generally contains about 0.8% or more benzyl isothiocyanate and a Lepidium fatty acid component of about 1% or more. When the aqueous solvent is 90 vol-% or more water, the first Lepidium composition has less than about 0.1% of benzyl isothiocyanate and less than about 2% Lepidium fatty acid component.

In a preferred embodiment, a first Lepidium composition having a Lepidium polysaccharide component of about 45% or more, a Lepidium fatty acid component between about 1% and about 2%, and less than about 1% each Lepidium sterol component and benzyl isothiocyanate is obtained by a suitably adapted first process that includes a reverse phase liquid chromatography process adapted to elute a first effluent containing a first Lepidium composition. In reverse phase liquid chromatography (RPLC), the column packing (stationary phase, or adsorbent) is non-polar, typically having a dipole moment of about 3 or less. Silica gel that has been treated to provide it with a bonded surface layer that is paraffinic in nature is an example of a useful stationary phase for reverse phase chromatography. Silica gels having permanently bonded $C_8$ to $C_{18}$ alkyl groups are commercially available as a stationary phase. For example, WP-Octadecyl from J. T. Baker Corp,, Phillipsburg, N.J., 08865. Reverse phase liquid chromatography columns are eluted with eluents of decreasing polarity which causes the more polar compounds loaded on a column to elute first.

Reverse phase liquid chromatography stationary phases of organic material are also known. Polymers of vinyl aromatic compounds, for example styrene, that are crosslinked with polyvinylic aromatic hydrocarbons, for example divinyl benzene, can be used as stationary phases for reverse phase liquid chromatography. These organic polymeric stationary phases are made by processes that yield small, extremely rigid, macroreticular particles. Crosslinked acrylic polymers are also useful as stationary phases for reverse phase liquid chromatography, as are polyvinyl alcohols (alkylated or non-alkylated). Suitable stationary organic phases for RPLC are commercially available. For example, styrenic and acrylic stationary phases are available from the Rohm and Haas Company, Philadelphia, Pa., under the trade name Amberlite®. Styreneic stationary phases are also available under the trade name Amberchrom® from Tossohass, Montgomeryville, Pa. Polyamide resins (e.g. nylons), polyester resins, and phenolic resins are also useful stationary phases for the reverse phase chromatography processes of the present invention.

Many organic solvents are suitable mobile phases, or eluents, for reverse phase liquid chromatography. Lower alcohols, such as methanol, ethanol, and propanol, as well as nitriles such as acetonitrile, are suitable as organic eluents. Lower aliphatic ketones such as acetone, methyl ethyl ketone, and diethyl ketone, as well as cyclic ethers such as tetrahydrofuran, can also be used. Dimethyl formamide, dimethyl sulfoxide, and alkyl esters of acetic acid such as ethyl acetate can also be used. Mixtures of such solvents in various proportions can be used when it is desired to elute or wash the column with solvents of varying polarity. Applicants have found that aqueous solvents that are mixtures of water and an alcohol, for example, methanol, ethanol, n-propanol, iso-propanol, n-butanol, and n-and sec-hexanol, are particularly useful as mobile phases or eluents for the RPLC processes of the present invention, which in certain embodiments are carried out using an eluent of variable composition. Thus, an elution volume which is a volume of aqueous solvent applied to the column, can be a gradient eluent having two or more gradient volumes, the composition of which can be the same or different, or the composition of the gradient eluent can be varied continuously during elution. The composition of the elution volume that is a gradient eluent can vary step-wise, linearly, sigmoidally, exponentially, logarithmically, parabolically, or hypyperbolically during elution. The limits of concentration of gradient eluents are determined by the concentration of polar organic solvent necessary to elute products from the stationary phase and by the requirement that the polar organic solvent be miscible to form a single phase at the required concentration.

In certain embodiments of the present invention the initial alcohol concentration in the elution volume is 10 volume percent (10 vol-%/o) or less and is increased as separation and purification proceeds.

The reverse phase liquid chromatography systems used to practice the present invention may be either preparative or analytical. Preparative columns have larger loading capacity and are typically larger in size.

With regards to the dimensions of the reverse phase liquid chromatographic column, the loading of the column, the temperature, and flow rate, one skilled in the art will know to vary these parameters based primarily upon practical considerations known in the art. For example, flow rates of the eluent are adjusted according to the column dimensions, the degree of separation desired, the particle size of the stationary phase, and the back pressure in the column. The separation is typically carried out at 20° C. to 30° C. However, a temperature up to about 45° C. can be used. The separation may be carried out at high pressure (500–200 psi) or moderate pressures (100–500 psi) or, preferably, at lower pressures (10–100 psi).

Prior to use, the reverse phase liquid chromatography column can be conditioned by eluting the column with a conditioning volume of a conditioning liquid, preferably an aqueous solvent, more preferably water. The conditioning volume is preferably between about 1 and about 10 column volumes.

The material to be treated is applied to the preferably conditioned reverse phase chromatography column as a solution, a slurry, or a loading concentrate obtained by evaporating an aqueous solvent, preferably alcohol, from an extraction composition containing the product. If the product to be treated is solid, it may be mixed with a suitable solid carrier, for example treated or untreated silica gel, and the solid mixture placed on top of the solid support. Loading of the column is accomplished by eluting the solution, slurry, or loading concentrate through the column; or, when the product to be treated is admixed with silica gel, by eluting the column with a loading elution volume. Preferably, elution of the solution, slurry, loading concentrate, or loading elution volume is followed by elution with a washing elution volume comprising an aqueous solvent having the same composition as the aqueous solvent of the solution, slurry, or loading concentrate used to load the column stationary phase. The washing elution volume, when one is used, is preferably between about 1 and about 10 column volumes.

Starting material for this adapted first process is a first Lepidium composition made by the previously described first process in which the aqueous solvent is an alcohol-water mixture having between about 65 vol-% and about 85 vol-%, preferably about 75 vol-% of alcohol, preferably SDA. The stationary phase of the RPLC column is a styrenic resin, preferably a crosslinked styrene-divinylbenzene resin such as Amberlite® XAD-16HP available from Rohm and Haas. The first Lepidium composition from a first process, combined with water (5–7 L per kg of first composition), is eluted through an RPLC column to apply the first composition to the column. The column is then eluted with an elution volume effective to elute a first effluent containing a first Lepidium composition, the solids component of which includes about 45% or more of a Lepidium polysaccharide component. Typically the elution volume contains aqueous solvent that is preferably water or an alcohol-water mixture having at least about 90 vol-% water and the elution volume amounts generally to 4 to 7, preferably 6, column volumes. The effluent is collected and concentrated to yield a first Lepidium composition having a Lepidium polysaccharide component of about 45% or more.

The first process can be further adapted to produce a second effluent by including, after elution of a first elution volume, the step of eluting a second elution volume that includes an aqueous solvent. Second Lepidium composition is obtained by concentrating the second effluent. In this or any other embodiment, the concentrating can be by any suitable means as know in the art such as evaporation, distillation, lyophilization, and the like. Generally, the second elution volume is typically to 4 to 10 column volumes. The second effluent contains a second Lepidium composition having between about 0.3% and about 12%, preferably between about 2% and about 10%, more preferably between about 5% and about 10% of benzyl isothiocyanate; between about 0.3% and about 2.7%, preferably between about 1% and about 2.5% of a Lepidium sterol fraction; and between about 10% to about 65%, preferably between about 10% and about 25% of a Lepidium fatty acid component.

In one embodiment of the adapted first process, the second elution volume has at least two gradient volumes, each of which contains an aqueous solvent. The identity or composition of the aqueous solvent in each of the two or more gradient volumes can be the game or it can be different. Preferably it is different. The second effluent resulting from the elution of the second elution volume can be fractionate collected into at least as many gradient fractions as there are gradient volumes eluted. The fractionate collected gradient fractions can be combined, or they can be maintained separately. The gradient fractions can be concentrated to obtain second Lepidium compositions. It will be apparent to one skilled in the art that the identity and amounts of constituents of second Lepidium compositions made by this process can be varied by varying the number and composition of gradient volumes eluted, the number and volume of gradient fractions that are fractionate collected, and the manner in which gradient fractions are combined.

In a preferred embodiment of the adapted first process, the second elution volume is an alcohol-water mixture having 70 vol-% and preferably 80 vol-% or more alcohol, preferably SDA. The second Lepidium composition obtained in this process contains between about 0.2% and about 10%, preferably between about 2% and about 5/%, of benzyl isothiocyanate; between about 0.15% and about 3%, preferably between about 0.2% and about 1%, of a Lepidium sterol component; between about 1% and about 65%, preferably between about 10% and about 25% of a Lepidium fatty acid component; and between about 0.3% and about 0.5% of a macamide component, wherein the macamide component comprises about 30% or more macamide B and 20% or more macamide C. Second Lepidium compositions typically have less than about 5%, preferably less than about 1%, of either a Lepidium polysaccharide component or a Lepidium amino acid component.

A second Lepidium composition can also be obtained from a second extraction composition from a second process. In a second process, residual Lepidium plant material that remains after separating the first extraction composition is contacted in a second contacting step with an aqueous solvent, preferably a mixture of an alcohol and water having about 80 vol-% or more, preferably about 90 vol-% or more alcohol, preferably SDA, to produce a second extraction composition or liquor. The process of contacting in the second contacting step can be the same as that in the first contacting step of a first process or it can be different. The liquor is separated from residual Lepidium plant material and concentrated to obtain a second Lepidium composition. The separating can be by any process known in the art; for example centrifugation, filtration, or decanting.

The second Lepidium composition obtained by a second process (MD-A) has between about 5% and about 9% of benzyl isothiocyanate, a Lepidium sterol component of between about 1% and about 3%, a Lepidium fatty acid component between about 10% and about 20%, and a macamide component of 10% or more. Generally, a Lepidium sterol component includes about 50% or more β-sitosterol and also contains stigmasterol and campesterol. Generally, a Lepidium fatty acid component contains between about 0.5% and about 1.2% 9,16-dioxo-10E,12E, 14E-octadecatrieneoic acid between about 1.5% and about 3.5% of 16-hydroxy-9-oxo-10E,12E,14E-octadecatrieneoic acid between about 30% and about 35% linoleic acid, and between about 15% and about 22% linolenic acid. Generally, a Lepidium fatty acid also contains oleic acid. In preferred embodiments, the second composition also contains about 0.2% or more of a macamide component, wherein the macamide component comprises 1% or less macamide A, about 10% or more macamide B, and about 20% or more macamide C.

The present invention also provides a third Lepidium composition that contains a mixture of a pharmaceutically acceptable excipient with a first Lepidium composition, a second Lepidium composition, or with both a first and second Lepidium composition. Pharmaceutically acceptable excipients are any materials that do not interfere with the pharmacological activity of the third composition or degrade the bodily functions of the animal to which it can be administered, but facilitate fabrication of dosage forms or actual administration of the composition; for example by improving palatability of oral dosage forms. Examples of pharmaceutically acceptable excipient include but are not limited to maltodextrin, calcium phosphate, and fused silica. Pharmaceutically acceptable excipients also include flavorants.

Third compositions of the present invention can be made, for example, by combining about 25% to about 50% (dry weight) of a first or second Lepidium composition of the present invention and about 75% to about 25% (dry weight) of one or more pharmaceutically acceptable excipients, combining this mixture with water (5 liter per kg of solids) and homogenizing the mixture. A Silverson Model 14 RT-A homogenizer (Silverson Corporation, East Longmeadow, Mass.) is an example of an apparatus suitable for carrying-out the homogenization. The homogenized composition is then dried to obtain a third Lepidium composition. The drying may be carried-out by any means as are known in the art; for example spray drying, oven drying, rotary vacuum drying, or lyophilization.

In yet other embodiments, the present invention provides novel amides of fatty acids, namely; N-benzyl octanamide (also called macamide A or MA-3), racemic and enantiomerically pure N-benzyl-16-hydroxy-9-oxo-10e,12e,14e-octadecatrienamide (also called macamide B or MA-S4), and N-benzyl 9,16dioxo-10e,12e,14e-octadecatrienamide (also called macamide C or MA-9). All of these N-substituted amides are members of the class macamides, as that term is used herein. The N-benzyl amides of the present invention, which are useful in the prevention or treatment of carcinomas, can be synthetically prepared, or obtained from Lepidium plant material, preferably *Lepidium meyenii*, by chromatographic processes. The chromatographic process is particular useful for obtaining enantiomerically pure N-benzyl-16(S)-hydroxy-9-oxo-10e,12e,1 4e-octadecatrienamide.

N-benzyl amides of the present invention can be synthetically prepared by various methods (See Barstaw, L. E. et al., J. Org. Chem., 36, 1305,(1971)). For example, N-benzyl amides of the present invention can be made by refluxing the corresponding carboxylic acid and benzyl amine with triphenylphosphene and bromotrichloromethane.

The N-benzyl amides of the present invention can be isolated from Lepidium plant material by c chromatographic process. Starting material for isolation of the N-benzyl amides of the present invention by chromatographic processes is a dry powder loading composition formed by mixing with silica gel (60–100 mesh) the residue from rotary vacuum concentration of an ethyl acetate extract of an aqueous suspension of a first Lepidium composition from a first process in which the aqueous solvent contains a mixture of about 75% SDA and about 25% water. The dry powder loading composition is applied to a chromatography column that is the eluted with a series of gradient volumes. The resulting gradient eluents are fractionate collected and compared by thin layer chromatography (TLC). Fractionate collected gradient eluents having similar TLC patterns are combined and combined fractions are further treated by column chromatography.

The methods of preventing or treating carcinomas, libido-related male sexual dysfunction, male impotence, and muscle fatigue comprise administering or dosing an effective amount of a composition, which can be a third Lepidium composition, that contains a first or second Lepidium composition, or both. The meaning of effective amount will be recognized by clinicians but includes an amount effective to either (1) reduce the symptoms of the disease or condition sought to be treated or prevented (i.e. cancer, sexual dysfunction), (2) induce a pharmacological change relevant to treating or preventing the disease sought to be treated or prevented, or (3) prevent the occurrence of the disease or condition.

The Lepidium compositions used in the method of the present invention can be administered by any route. Compositions of the present invention are administered alone, or are combined with a pharmaceutically-acceptable carrier or excipient according to standard pharmaceutical procedures. Preferably, Lepidium compositions are administered orally as a third Lepidium composition. For the oral mode of administration, the compositions of the present invention are used in the form of tablets, capsules, chewing gum, and the like. In the case of tablets, various disintegrants such as starch, and lubricating agents such as magnesium stearate and talc can be used.

Compositions of the invention can include pharmaceutically acceptable acid addition salts, particularly those obtained with mineral acids, for example hydrochloric or hydrobromic acid. However, organic acids, for example tartaric acid, can also be used.

The amount dosed will depend upon the composition used and the disease or condition to be treated or prevented. Generally, the compositions are dosed at between 0.1 g and 10 g per kg of body weight per day.

The present invention is illustrated by the following non-limiting examples.

EXAMPLE 1

In this and other examples, HPLC analysis of Maca product were performed on a Hewlett Packard Series 1100 HPLC using an phenomenex, Luna C-8 column. GC/MS analysis of Maca product was performed on an BP-5973 MSD using a Supelco SAC-5 capillary column.

Roots of *Lepidium meyenii* (4.6 Kg) were cut to a nominal dimension of about 1 cm and contacted with an aqueous solvent (75 vol-% SDA and 25 vol-% water, 25 L per kg root) at 45° C. by percolation. Decoction was separated from the plant material and concentrated to yield a first composition (2.1 Kg), denoted NE, having a solids content of 77% (i.e. 1.6 Kg on a dry basis). The solids component included, based on the solids present; 0.89% benzyl isothiocyanate, 0.079% of a Lepidium sterol component, 1.46% of a Lepidium fatty acid component, 8.72% of a Lepidium amino acid component, and 41.9% of a Lepidium polysaccharide component.

EXAMPLE 2

Roots of *Lepidium meyenii* (500g) were reduced in size to a nominal dimension of 0.5 cm and contacted with 14 L water by percolation. The aqueous phase was separated from residual plant material and evaporated to dryness to obtain 20 g of a tacky product. The tacky product had a Lepidium sterol component of <0.01%, a Lepidium fatty acid component of <0.1%, a Lepidium amino acid component of 9%, and A Lepidium polysaccharide component of 44%.

EXAMPLE 3

The residual plant material from example 2 was contacted with 15 L of 100% SDA by percolation to form a liquor. The liquor was separated and concentrated to yield 10 g of a second Lepidium composition having 7.8% benzyl isothiocyanate, a Lepidium sterol component of 1.8%, a Lepidium fatty acid component of 22%, and a macamide component of 12%. No Lepidium amino acid component was found in the composition.

EXAMPLE 4

A first Lepidium composition (1.6 Kg) obtained according to the process of example 1 (i.e. NE), was slurried with water (8.8 L per kg of dry NE) for about 30 min. The slurry was applied to a RPLC column (15 cm.×100 cm packed with Amberlite® XAD-16 (Rohm and Haas Co.) that had been preconditioned with 20 column volumes of water. The column was eluted with a first elution volume (6 column volumes) of 100 vol-% water. The resulting first effluent was collected and evaporated to dryness to yield 1.5 g of a first Lepidium composition having 0.15% benzyl isotiocyanate, 0.07% of a Lepidium sterol component, 1.8% of a Lepidium fatty acid component, 10% of a Lepidium amino acid component, and 48% of a Lepidium polysaccharide component. The composition had less than 1% of a macamide component.

EXAMPLE 5

The RPLC of example 4 was eluted with a second elution volume (6 column volumes) that was made-up of 100% SDA. The resulting effluent was collected and evaporated to dryness to yield 162 g of a second Lepidium composition having 4.1% benzyl isothiocyanate, 0.4% of a Lepidium sterol component, 12% of a Lepidium fatty acid component, 4.4% of a macamide component, and no Lepidium amino acid component or Lepidium polysaccharide component.

EXAMPLE 6

A first Lepidium composition (1.6 Kg NE on a dry basis), obtained according to the method of example 1, was slurried with water (6.3 L per kg of first Lepidium composition) for about 30 min. The slurry was applied to a RPLC column (15 cm×100 cm) packed with Amberlite® XAD-16 resin (Rohm and Haas Co) that had been preconditioned with about 20 column volumes of water. The column was eluted with a first elution volume of 4 column volumes of water. The column was then eluted with a second elution volume that was made-up of five gradient volumes, each having a volume equal to 4 column volumes and each made-up of a mixture of SDA and water. The gradient fractions had, respectively, 20 vol-%, 40 vol-%, 60 vol-%, 80 vol-%, and 100 vol-% SDA. The gradient fractions corresponding to each of the gradient volumes were fractionate collected and analyzed (HPLC and GC). The gradient fractions were free of both an Lepidium amino acid component and a Lepidium polysaccharide component. The gradient fractions contained other components as set-out below in Table 1.

TABLE 1

Content of Various Lepidium Components in Gradient fractions of a RPLC Process.

|  | Fr*. M-F1 | Fr. M-F2 | Fr. M-F3 | Fr. M-F4 | Fr. M-F5 |
| --- | --- | --- | --- | --- | --- |
| Benzyl isothiocyanate - % | 0.7 | 0.4 | 2.5 | 2.5 | 5.8 |
| Lepidium sterol component - % | 0.36 | 0.18 | 0.67 | 0.87 | 2.2 |
| Lepidium fatty acid component - % | 0.29 | 0.14 | 0.54 | 0.70 | 1.8 |
| Macamide component - % | 0 | 0 | 0.2 | 1.6 | 0 |

*Fr. = fraction

The gradient fractions were combined and concentrated to yield 125 g of a second Lepidium composition having 2.3% benzyl isothiocyanate, 0.8% of a Lepidium sterol component, 17.2% of a Lepidium fatty acid component, and 0.4% of a macamide component.

EXAMPLE 7

The tests were performed according to the MT assay (See, Mosmann, T., *J. Immun. Meth.*, 6, 55(1983).

Cells were planted in 96 well flat bottom plates with low evaporation lids. Three cell lines per plate were seeded in 0.2 ml medium per well. Each cell line was planted at the optimum concentration for its particular growth rate: HT-29 and A-549, 5000 c/ml; MCF-7, 15000 c/ml; A498, 10,000 c/ml; PC-3, 15000 c/ml; and PACA-2, 10,000 c/ml. Products were tested at various dilutions (at least ten) to determine the $ED_{50}$.

The results are given in table 2

TABLE 3

Individual Bodyweight and Dosage.

| Animal No. | Sex | Initial | Day 7 | Day 14 | Dose* |
|---|---|---|---|---|---|
| 5025 | M | 246 | 309 | 349 | 1.6 |
| 5026 | M | 236 | 297 | 332 | 1.6 |
| 5027 | M | 251 | 340 | 383 | 1.7 |
| 5028 | M | 263 | 341 | 379 | 1.7 |
| 5029 | M | 242 | 308 | 335 | 1.6 |

TABLE 2

6-Cell Line Clinical Test Results, Expressed as $ED^{50}$ values (in μg/ml)

| Sample Code | Sample Description | Kidney A-498 | Prostate PC-3 | Pancreatic PACA-2 | Lung A-549 | Breast MCF-7 | Colon HT-29 |
|---|---|---|---|---|---|---|---|
| MA-1 | | 24.88 | 85.77 | 17.66 | 28.66 | >100 | 54.65 |
| MA-2 | | 9.08 | 4.05 | 3.06 | 17.97 | 29.33 | 22.97 |
| MA-3 macamide A | | 5.83 | 6.42 | 4.33 | 7.57 | 28.45 | 19.02 |
| MA-7 | | 51.79 | 64.22 | 31.62 | 63.37 | 93.49 | 61.55 |
| SY-197A | Maca NE | 56.85 | 94.67 | 37.60 | 56.99 | 97.51 | 64.17 |
| M-F1 | Purified Product Fraction #1 (20% SDA) | >100 | >100 | >100 | >100 | >100 | 49.24 |
| M-F2 | Purified Product Fraction #2 (40% SDA) | >100 | >100 | >100 | >100 | >100 | 40.57 |
| M-F3 | Purified Product Fraction #3 (60% SDA) | >100 | >100 | >100 | >100 | >100 | 40.57 |
| M-F4 | Purified Product Fraction #4 (80% SDA) | 38.29 | 29.59 | 29.43 | 17.03 | 34.41 | 6.10 |
| M-F5 | Purified Product Fraction #5 (100% SDA) | 26.54 | 20.66 | 24.94 | 25.37 | 32.57 | 3.09 |
| M-F2–5 | Purified Product Fraction #2~5 | >100 | 30.96 | 37.56 | 33.26 | 56.18 | 41.08 |
| Adriamycin | | $3.59 \times 10^{-3}$ | $2.81 \times 10^{-2}$ | $5.22 \times 10^{-3}$ | $3.16 \times 10^{-3}$ | $1.07 \times 10^{-1}$ | $2.20 \times 10^{-2}$ |

EXAMPLE 8

Ten healthy rats were dosed by oral gavage with 5 g of third Lepidium composition per kilogram of body weight. The animals were observed for signs of gross toxicity for 14 days. The body weights of the animals were checked on the $7^{th}$ and $14^{th}$ days. Body weight data is collected in Table 3. Gross necropsy findings at terminal sacrifice were unremarkable.

TABLE 3-continued

Individual Bodyweight and Dosage.

| Animal No. | Sex | Initial | Day 7 | Day 14 | Dose* |
|---|---|---|---|---|---|
| 5030 | F | 197 | 230 | 253 | 1.3 |
| 5031 | F | 200 | 231 | 261 | 1.3 |
| 5032 | F | 185 | 227 | 247 | 1.2 |
| 5033 | F | 193 | 230 | 250 | 1.3 |
| 5034 | F | 186 | 231 | 249 | 1.2 |

*Administered as a 60% w/w suspension in distilled water. Specific Gravity = 1.259 g/ml.

EXAMPLE 9

Sufficient mice (22±1.5 g) were dosed for 21 days with 1 g of either of two third Lepidium compositions. One group (group I) was dosed with a third Lepidium composition made with a first Lepidium composition obtained according to example 1. A second group (group II) was dosed with a third Lepidium composition made with a second Lepidium composition obtained according to example 5. One hour after the dosing on the $21^{st}$ day, each mouse was individually placed in water (25±2° C.) and observed. The elapsed time at which a mouse remained submerged. The results are collected in Table 4.

TABLE 4

Muscle Fatigue Results.

| Group | Animal Number (n) | Duration of Swim Time In Seconds (mean ± SD) | p |
|---|---|---|---|
| Control Group | 15 | 110.07 ± 2.58 | |
| Group I | 15 | 124.07 ± 3.30 | <0.01 |
| Group II | 15 | 144.13 ± 3.52 | <0.01 |

EXAMPLE 10

Sufficient male mice (22±1.5 g; 15 per group) were dosed by oral gavage for 21 days with 1 g/day of either of two third Lepidium compositions. Male mice in one group (group-I) were dosed with a third Lepidium composition made with a first Lepidium composition obtained according to example 1. Male mice in a second group (group II) were dosed with a third Lepidium composition made with a second Lepidium composition obtained according to example 5. A control group received no third Lepidium composition. Mice were ear-tagged or color coded for identification. On the $21^{st}$ day, ½ hour after dosing, each male was placed in a cage with two mice and observed under darkroom conditions. The mice were observed for three hours and the number intromissions were recorded. Intromission was indicated by a characteristic rearward lunge by the male terminating coitus. Results are summarized in table 5 below.

TABLE 5

Intromission Results.

| Group | Number of Intromissions (mean ± SD) | p |
|---|---|---|
| Control | 16.33 ± 1.78 | |
| Group I | 46.67 ± 2.39 | <0.01 |
| Group II | 67.01 ± 2.55 | <0.01 |

EXAMPLE 11

Testectomies were performed on a sufficient number of male rats using pentobarbital, 45 mg/kg, as anesthetic. Rats were treated postoperatively for 3 days with sodium penicillin, 2,000 U/kg. Rats were ear-coded and color-coded for identification and divided into 7 groups. Three groups of 10 rats each (Set A) were dosed by oral gavage for 21 days with a third Lepidium composition made with a first Lepidium composition obtained according to example 1. Rats in each of the three groups received a different dosage. A second set of three groups of 10 rats each (Set B) were dosed for 21 days with a third Lepidium composition made with a second Lepidium composition obtained according to example 5. Rats in each of the three groups received a different dosage. A control group of 10 rats received no third Lepidium composition.

On the $21^{st}$ day, ½ hour after dosing, rats were restrained and an electric pulse of 20 V was applied to the penis using an electrode of a YSD4G multifunction instrument. The time to achieve full erection was monitored. Results are collected in table 6 below.

TABLE 6

Incubation Period of Erection (IPE) in Testicle-Removed Rats with Oral Administration of M-PE and MC-A PE.

| Group | Dose (mg/kg) | Animal Number (n) | Incubation Period of Erection in Seconds (mean ± SD) |
|---|---|---|---|
| Surgical Group | | 10 | 137.4 ± 81.6 |
| Set A | | | |
| Low dose | 45 | 10 | 121.4 ± 51.3 |
| Middle dose | 180 | 10 | 54.0 ± 25.8 |
| High dose | 1800 | 10 | 90.5 ± 80.2 |
| Set B | | | |
| Low dose | 45 | 10 | 71.2 ± 32. |
| Middle dose | 180 | 10 | 73.2 ± 39. |
| High dose | 1800 | 10 | 80.9 ± 85.1 |

EXAMPLE 12

The N-benzyl amides of the present invention can be isolated from Lepidium plant material by chromatographic process. Starting material for isolation of the N-benzyl amides of the present invention by chromatographic processes is a dry powder loading composition formed by mixing with silica gel (60–100 mesh) the residue from rotary vacuum concentration of an ethyl acetate extract of an aqueous suspension of a first Lepidium composition from a first process in which the aqueous solvent contains a mixture of about 75% SDA and about 25% water. The dry powder loading composition is applied to a silica gel column (130–270 mesh) and the column is then eluted with, in sequence, five elution volumes, each about 8 column volumes that contain mixtures of n-hexane and acetone in the following ratios (vol-% n-hexane:vol-% acetone): 10:1, 5:1, 2:1, 1:1, and 0:1. The column effluent is divided into 18 fractions. The $25^{th}$ through $27^{th}$ liter of effluent make-up a sixth fraction. The $41^{st}$ through $49½^{th}$ liter of effluent make-up a ninth fraction. The $63^{rd}$ through $70^{th}$ liter of effluent make-up a twelfth fraction.

N-benzyl octanamide can be obtained by chromatographic treatment of the sixth fraction by treating the sixth fraction on a silica gel column using a n-hexane-acetone mobile phase (3:1). N-benzyl octanamide can be isolated from the effluent (all of it? What part?) by removing mobile phase from the effluent.

N-benzyl octanamide has the following physical and spectroscopic properties: white powder, m.p.=76–78° C.; UV$\lambda_{max}$(MeOH)=213 nm ($\epsilon$=11007). IR$_{\gamma KBr}$(cm$^{-1}$): 3407, 2938, 2859, 1628, 1544, and 1451. Molecular Formula:

$C_{15}H_{23}NO$. EI MS m/z [M+]: 162, 149, 148, 106, 91, 77, and 57. $^1H$ and $^{13}C$ NMR ($CDCl_3$):2.17 (2H, t, J=7.2 Hz, H-2), 1,59 (sH, m, H-3), 1.28 (8H, m, H-4, 4, 6, 7'), and 5.65 (1H, br s, NH). The structure of N-benzyl octanamide can be represented, without regard to stereochemistry, as:

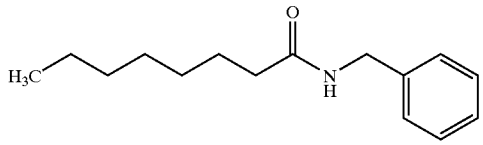

N-benzyl-9,16-dioxo-10E,12E,14E-octadecatriene amide (MA-9, macamide C) can be isolated from the ninth fraction by further chromatographic treatment of the fraction on a silica gel column using 30 elution volumes of hexane/acetone as mobile phase. Fractions 15–20 (i.e. effluent from elution volumes 15–20) were further treated by preparative HPLC (Dynamax-60A column) using acetonitrile-water gradient eluent (5:95 to 95:5 vol. ratio, acetonitrile:water) to obtain N-benzyl-9,16oxo-10E,12E,14E-octadecatrienamide. The structure of macamide C can be represented, without regard to stereochemistry, as:

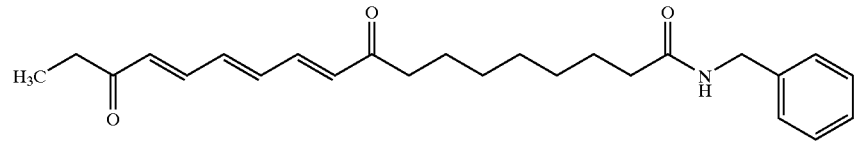

N-benzyl-9,16-dioxo-1E,12E,14E-octadecatrienamide has the following physical and spectroscopic properties: Light yellow powder, m.p.=115–116° C.; $UV\lambda_{max}$(MeOH)= 317nm ($\epsilon$=13847). $IR_{\gamma KBr}(cm_{-1})$:3297,2930, 1715, 1680, 1637, 1602, 1544, 1112, and 1003. Molecular formula (elemental analysis): $C_{25}H_{33}NO_3$. EI MS m/z, 395; [M+]; 366, 338, 260, 163, 106, 91, and 77. The structure of mamamide B can be represented, without regard to stereochemistry, as:

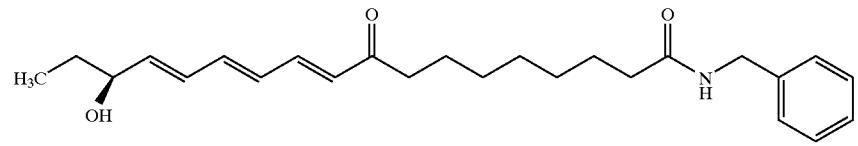

N-benzyl-16(S)-hydroxy-9-oxo-10E,12E,14Eoctadecatrienamide (MA-S-4, macamide B) can be isolated from the twelfth fraction by preparative HPLC (Dynamax C-18 column) of the twelfth fraction using an acetonitrile-water gradient mobile phase (10:90 to 90:10 volume ratio acetonitrile:water).

N-benzyl-16(S)-hydroxy-9-oxo-10E,12E,14E-octadecatrienamide has the following physical and spectroscopic properties: White powder, m.p. 95–96° C., $UV\lambda_{max}$(MeOH)=314 mn ($\epsilon$=36392). $IR_{\gamma KBr}(cm^{-1})$:3368, 2930, 2850, 1677, 1622, 1598, 1583, 1240, 1108, and 1057. Molecular formula (elemental analysis): $C_{25}H_{35}NO_3$. CI MS m/z, 397.

Experimental details are given below.

Contacting of *Lepidium meyenii* was carried out by percolation accordibg to the following procedure. The roots were grounded into pieces shorter than 3 cm in length. The ground material was then equally divided and loaded into three similarly-sized percolators. For the first cover, 75% SDA was loaded into each percolator at a ratio of 4.2:1 (volume of solvent in liter: weight of material in kg). After the solution had been circulated for 5 hr. at room temperature, the extract was transferred to a still and concentrated in vacuo at a temperature below 65° C. For the second cover, fresh 75% SDA was added into percolator #1. After the solution had been circulated for 5 hrs, the extract was transferred to percolator #2. After the solution in percolator #2 had been circulated for 5 hrs, the extract was transferred to percolator #3. The solution in percolator #3 was circulated for 5 hrs and the extract was transferred to the same still (for the first cover) and concentrated in vacuo at a temperature below 65° C. The procedure as described above was repeated three more times to give a total of 5 covers, which were concentrated until the residue had a total solid dry base of 72.9 %.

3.5 kg of the extract was suspended in 1.8 liter water, and extracted with EtOAc (3×1000 ml). The combined extract was concentrated in vacuo at 40° C. to dryness (241 g). The residue was mixed with silica gel (60–100 mesh, 200 g) and airdried, and then applied to a silica gel column (7.5×60 cm, 800 g, 130–270 mesh) eluted with five 20 L hexane/acetone gradient volumes (10:1-5:1-2: 1-1:1-0:1, total volume 100 l). Every 500 ml was fractionate collected and concentrated, a total of 200 portions were collected. All portions were analyzed by thin layer chromatography (TLC) and portions having similar TLC patterns were combined to give 18 fractions. The sixth fraction (1.8 g from 25th through 27th liters collected) was chromatographed over silica gel (60 g) using hexane/acetone (3:1, 2l) as the mobile phase to give 25 mg of N-benzyloctanamide (macamide A or MA-3). The ninth fraction (3.4 g; 41st through 49th liters collected) was initially separated over silica gel column (120 g, 130–270 mesh) into 30 fractions (100 ml each). The fractions (frs 15–20) which mainly contained N-benzyl-9,16oxo-10E, 12E,14E-octadecatrienamide (MA-9 or macamide C) were combined and subjected to preparative HPLC (column:

Dynamax-60A C18, 2.14 I 25 cm i.d., 8 μm) using Acetonitrile/0.1% HOAc gradient system (0–60 min, from 5% Acetonitrile to 95% Acetonitrile) as the mobile phase with a flow rate of 10 ml/min to give 10 mg of MA-9. The twelfth fraction (10 g) was chromatographed on silica gel eluting with $CHCl_3$/EtOAc (2:1, 200 ml per fraction, total 5 l). The fractions (10–15) mainly contained N-benzyl-16(S)-hydroxy-9-oxo-10E,12E,14E-octadecatrienamide (MA-S4 or macamide B) were combined and purified by preparative HPLC run on a Dynamax C-18 column using an acetonitrile/0.1% HOAc gradient system (0–60 min, from 10 % Acetonitrile to 90 % Acetonitrile) as eluent to give 33 mg of MA-S-4.

MA-3 showed the similar UV and IR spectra as those of N-benzyl-hexadecamide (MA-1) indicating that MA-3 was a fatty amide. The $^{13}C$ resonance of a carbonyl at δ173.2 supported the amide structure. The $^1H$ signals at δ4.41 (2H, d, J=4.4 Hz), 5.71 (br s), 7.25 (5H), and $^{13}C$ signals at δ127.5 (1C, d), 127.8 (2C, d), 128.7 (2C, d), and 43.6 (1C, t) suggested that MA-3 had a same amine group as that of MA-1. The molecular fromula, $C_{15}H_{23}NO$, was derived from the EI mass spectrum and indicated five degrees of unsaturation. The benzene ring and the amide group accounted for all the five unsaturation degrees. Therefore, the fatty acid moiety was acyclic.

The $^1H$ NMR spectrum displayed a terminal methyl group at δ0.86, and the COSY spectrum revealed coupling of this group with an unresolved eight proton proton complex at δ1.28. One methylene group was observed as triplet (J=7.2 Hz) at δ2.17, indicating that it was adjacent to the carbonyl group. In the COSY spectrum, this methylene group was found to be coupled to another methylene group at δ1.59 which in turn was coupled to the methylene signals at ca δ1.18. It was suggested that the fatty acid moiety had eight carbons. Treatment of this compound by 6N HCl followed by $CH_2N_2$ gave methyl caprylate that was identified by GC-MS analysis. Thus, the fatty acid moiety was unambiguously determined as octanoyl. Therefore, MA-3 was identified as N-benzyl-octanamide, also designated herein as macamide A.

Compound N-benzyl-16(S)-hydroxy-9-oxo-10E,12E, 14E,-octadecatrienamide MA-S4) showed maximum absorption at 314 nm (ε=36392), suggesting a conjugated trienone. It possessed a molecular formula $C_2H_{35}NO_3$ by mass spectrum and the NMR data (Table 1), which requires eight unsaturation equivalents. The $^1H$ signals at δ4.73 (2H, d, J=6 Hz), 9.00 (br s, NH), 7.35 (5H), and $^{13}C$ signals at δ127.3 (1C, d), 128.1 (2C, d), 128.9 (2C, d), and 43.4 (1C, t) suggested that MA-S-4 had the same amine group as that of MA-1 and MA-3. The $^{13}C$ NMR spectrum revealed two carbonyl, a benzene ring and three other olefins, accounting for all the degrees of unsaturation and indicating MA-S4 had an acyclic fatty acid moiety. The DEPT and $^{13}C$ NMR spectra showed the signals for total eighteen carbons, including one methyl, eight methylenes, seven methines, two quaternary carbons for the fatty acid moiety. Thus, a $C_{18}$ fatty acid moiety was proposed.

The COSY, with aid of TOSCY, assigned the all proton resonances. The isolated terminal methyl group at δ1.07 (H-18) and methylene groups at δ2.45 (H-2) and 2.54 (H-8) were chosen as the starting points for the analysis of COSY and TOCSY. The correlations between H-18 (δ1.07) and H-17 (δ1.74), H-17 and H-16 (δ4.41), H-16 and H-15 (δ6.25), H-15 and H-14 (δ6.71), H-14 and H-13 (6.82), H-13 and H-12 (δ6.44), H-12 and H-11 (δ7.47), H-11 and H-10 (δ6.33) led to the assignment of the protons continuing from H-18 to H-10. The correlations between H-2 and H-3 (δ1.63), H-3 and H4 (δ1.24), H-8 and H-7 (δ1.83), H-7 and H-6 (δ1.34) led to the assignment of protons from H-2 to H-8 except for H-5. The overlaped proton systems at (δ1.24) contained four protons. Hence, two protons were assigned to H-5 (δ1.24). In HMBC spectrum, the long-range correlations between H-2 (δ2.45) and C-1 (δ173.1), and H-8 (2.54) and C-9 (δ200.0 ) confirmed the assignment of H-2 and H-8. The $^{13}C$ NMR data were then assigned by HSQC spectrum. The $^{13}C$ resonance of C-16 at δ72.7 indicated that one hydroxy group was attached to C-16.

The large couplings between the olefinic protons ($J_{10,11}$= 15.6 Hz, $J_{12,13}$=14.0 Hz, and $J_{14,15}$=15.6 Hz) revealed that three of the double bonds had E configurations. The absolute stereochemistry of C-16 secondary alcohol was determined by optical rotations which were of the same sign and magnitude ($[\alpha]_D$+) as those of coalital ($[\alpha]_D$+21, °, C.=0.63, $Me_2CO$) and 16(S)-hydroxy-9-oxo-10E,12E,14E,-octadecatrienoic acid ($[\alpha]_D$+11.7°, C.=0.2, $Me_2CO$), assigning a S configuration to C-16. The stereochemistry of coalital was determined by exciton chirality method reported by Bernart et al., J. Nat. Prod. 56:245(1993)).

Therefore, MA-S4 was determined to be N-benzyl-1 6(S)-hydroxy-9-oxo-10E,12E,14E-octadecatrienamide.

Compound N-benzyl-9,16-dioxo-10E,12E,14E-octadecatrienamide (MA-9) was isolated as a light yellow powder, m.p. 115–6° C. The UV spectrum showed maximum absorption at 317 nm (ε=13847), suggesting a conjugated trienone. The strong absorption bands at 2950 (aliphatic), 1715, 1680 (conjugated ketone), 3297, 1640, 1545 (amide), and 1003 $cm^{-1}$ (trans double bond) in the IR spectrum indicated that this compound was a fatty amide. The EI mass spectrum of MA-9 showed a molecular ion peak at m/z 395 consistent with the molecular formula $C_{25}H_{33}NO_3$. The $^{13}C$ resonance of the carbonyl carbon at δ173.3 favored that MA-9 was a fatty amide.

The $^1H$ signals at δ4,62 (2H, d, J=4.4 Hz), 8.83 (br s), 7.30 (5H), and $^{13}C$ signals at δ127.6 (1C, d), 128.4 (2C, d), 129.2 (2C, d), and 43.6 (1C, t) suggested that MA-9 had a same amine group as those of MA-1, MA-3 and MA-S4. The intense fragment ion peaks at m/z 91 and 106 supported the above inference.

All proton and carbon signals of the fatty acid moiety were unambiguously assigned using COSY, TOCSY, HMQC and HMBC techniques. The isolated terminal methyl group at δ1.01 (H-18), methylene groups at δ2.38 (H-2) and 2.50 (H-8), and olefinic protons for H-10 at δ6.30 and H-15 at δ6.34 were chosen as the starting points for the analysis of COSY and TOCSY. The methyl group (Me-18) were coupled with H-17 (δ2.61). The correlations between H-2 (δ2.38) and H-3 (δ1.62), H-8 (δ2.50) and H-7 (δ1.23) were observed. The correlations between H-3 and H4 (δ1.19), H-7 and H-6 (δ1.19) were observed. The proton complex at δ1.19 had six protons. The H-5 signals were regarded to account the left two protons. The correlations between H-10 (δ6.30) and H-11 (δ7.30), H-15 (δ6.34) and H-14 (δ7.30), H-11 and H-12 (δ6.68), H-14 and H-13 (δ6.68) confirmed the triene structure.

In HMBC, the correlations between H-2 (δ2.33) and C-1 (δ173.3), H-8 (δ2.56) and one ketone (C-9, δ200.5) confirmed the assignment of H-2 and H-8. The correlation between H-17 (δ2.61) and another ketone (C-16, δ200.3) confirmed the position of another ketone at C-16. The positions of the two ketone groups were supported by the daughter ion peaks observed in the EI mass spectrum. The ions at m/z 366 and 338 derived from the cleavage of C-17-C16 bond, and C-16-C-15 bond, respectively, indicated that a ketone was located at C-16. The ions at m/z 135, 163 and 260 derived from the rupture of C-9-C-10 bond and C-8-C-9 bond, respectively, revealed another ketone at C-9.

The double bonds at C-10 and C-14 were determined to be E configurations based on the large coupling constants ($J_{10,11}$=15.3 Hz, and $J_{15,14}$=15.3 Hz). Because the multiplets of H-11, H-12, H-13 and H-14 are not first order, and may be AA'BB' system, they do not display substantive couplings each other. The configuration of the double bond at C-12 could not be determined by coupling constant. However, it might be suggested to be E configuration based on the inference that MA-9 be a oxidized product of MA-S4.

Therefore, MA-9 was determined to be N-benzyl-9,16 dioxo-10E,12E,14E-octadecatrienamide. MA-9 is a new compound and named macamide C.

What is claimed:

1. A method of treating sexual dysfunction in an animal, comprising: administering a sexual dysfunction treating effective amount of an isolated composition derived from an aqueous solvent extract of *Lepidium meyenii* root to an animal in need of treatment for sexual dysfunction said isolated composition being substantially free of cellulose and comprising:

a) between about 5% and 9% of benzyl isothiocyanate, b) between about 1% and about 3% of Lepidium sterol component, c) between about 20% and about 30% of a Lepidium fatty acid component, and d) about 10% or more of macamide component.

2. The method of claim 1, wherein the animal is a human.

3. The method of claim 1, wherein the isolated composition further comprises a pharmaceutically acceptable excipient.

4. The method of claim 1, wherein the administration is oral administration.

5. The method of claim 1, wherein the animal is a male animal and the sexual dysfunction is sub-normal libido.

6. The method of claim 1, wherein the animal is a male animal and the sexual dysfunction is impotence.

7. The method of claim 1, wherein the macamide component comprises N-benzyloctanamide having the chemical formula $C_{15}H_{23}NO$.

8. The method of claim 1, wherein the macamide component comprises N-benzyl-16(R,S)-hydroxy-9-oxo-10E,12E,14E-octadecatrieneamide having the chemical formula $C_{25}H_{35}NO_3$.

9. The method of claim 1, wherein the macamide component comprises N-benzyl-16(S)-hydroxy-9-oxo-10E,12E,14E-octadecatrieneamide having the chemical formula $C_{25}H_{35}NO_3$.

10. The method of claim 1, wherein the macamide component comprises N-benzyl-9,16-dioxo-10E,12E,14E-octadecatrieneamide having the chemical formula $C_{25}H_{33}NO_3$.

* * * * *